US008703158B2

(12) United States Patent
Brew et al.

(10) Patent No.: US 8,703,158 B2
(45) Date of Patent: Apr. 22, 2014

(54) THEOBROMINE FOR THE TREATMENT OF COUGH

(75) Inventors: John Brew, London (GB); Robin Mark Bannister, London (GB)

(73) Assignee: Biocopea Limited, London (GB)

( * ) Notice: Subject to any disclaimer, the term of this patent is extended or adjusted under 35 U.S.C. 154(b) by 0 days.

(21) Appl. No.: 13/376,079

(22) PCT Filed: Jun. 15, 2010

(86) PCT No.: PCT/GB2010/050997
§ 371 (c)(1),
(2), (4) Date: Feb. 6, 2012

(87) PCT Pub. No.: WO2010/146394
PCT Pub. Date: Dec. 23, 2010

(65) Prior Publication Data
US 2012/0128738 A1 May 24, 2012

(30) Foreign Application Priority Data
Jun. 16, 2009 (GB) .................................. 0910375.5

(51) Int. Cl.
*A61K 9/02* (2006.01)
*A61K 9/14* (2006.01)
*A61P 11/14* (2006.01)
*C07D 473/10* (2006.01)

(52) U.S. Cl.
USPC .............................. 424/400; 424/46; 514/849

(58) Field of Classification Search
USPC ........................................................ 424/400
See application file for complete search history.

(56) References Cited

U.S. PATENT DOCUMENTS

| 6,348,470 | B1 | 2/2002 | Korbonits | |
| 2004/0202677 | A1 | 10/2004 | Hopkins et al. | |
| 2004/0204440 | A1* | 10/2004 | Staniforth et al. | 514/295 |
| 2005/0220897 | A1 | 10/2005 | Hack et al. | |
| 2006/0148837 | A1 | 7/2006 | Giordano et al. | |
| 2008/0003280 | A1 | 1/2008 | Levine et al. | |
| 2008/0085312 | A1 | 4/2008 | Wilson | |
| 2008/0176955 | A1 | 7/2008 | Heck et al. | |
| 2008/0220078 | A1 | 9/2008 | Morton | |
| 2009/0136427 | A1* | 5/2009 | Croft et al. | 424/9.2 |
| 2012/0252824 | A1 | 10/2012 | Brew | |

FOREIGN PATENT DOCUMENTS

| DE | 44 20 708 | 12/1995 |
| EP | 2050435 | 4/2009 |
| GB | 2 114 001 | 8/1983 |
| GB | 2 284 761 | 6/1995 |
| GB | 2424185 | 9/2006 |
| GB | 2 442 828 | 4/2008 |
| JP | 2003-128549 | 5/2003 |
| WO | 89/03213 | 4/1989 |
| WO | 95/07103 | 3/1995 |
| WO | 98/42322 | 10/1998 |
| WO | WO 98/42322 | 10/1998 |
| WO | 00/00212 | 1/2000 |
| WO | 00/30715 | 6/2000 |
| WO | WO 2006/059152 | 6/2006 |
| WO | WO 2006059152 A2 * | 6/2006 |
| WO | 2008/002514 | 1/2008 |
| WO | WO 2009019598 A2 * | 2/2009 |
| WO | 2010/146394 | 12/2010 |
| WO | 2011/058373 | 5/2011 |
| WO | 2011/058374 | 5/2011 |
| WO | 2011/073646 | 6/2011 |
| WO | 2011/073647 | 6/2011 |
| WO | 2012/025761 | 3/2012 |
| WO | 2013/004999 | 1/2013 |

OTHER PUBLICATIONS

"Abstracts: Presented at Poster Sessions," Annals of Allergy, Asthma & Immunology, Arlington Heights, IL, US, vol. 102, No. 1, Jan. 1, 2009, pp. A23-A128.
Database WPI, Week 200308, Thomson Scientific, London, GB, AN 2003-078587 & JP 2002-193839 (Meiji) Jul. 10, 2002.
Database WPI, Week 200343, Thomson Scientific, London, GB, AN 2003-451953 & JP 2003-055258 (Rohto) Feb. 26, 2003.
Database WPI, Week 200573, Thomson Scientific, London, GB, AN 2005-704785 & CN 1 593 451 (Yang X) Mar. 16, 2005.
Dicpinigaitis et al., Currently available antitussives. Pulmonary Pharmacology & Therapeutics, Academic Press, GB, vol. 22, No. 2, Apr. 1, 2009, pp. 148-151.
International Search Report for PCT/GB2010/050997 filed on Jun. 15, 2010.
International Search Report for PCT/GB2010/051895 filed on Nov. 12, 2010.
International Search Report for PCT/GB2010/051896 filed on Nov. 12, 2010.
International Search Report for PCT/GB2010/052085 filed on Dec. 14, 2010.
International Search Report for PCT/GB2010/052086 filed on Dec. 14, 2010.
International Search Report for PCT/GB2011/051610 filed on Aug. 25, 2010.
International Search Report for PCT/GB2012/050816 filed on Apr. 13, 2012.
Minamizawa, Kiyoshi et al., Effect of d-psuedophedrine on cough reflex and its mode of action in guinea pigs. J. Pharmacological Sciences, vol. 102, No. 1, Sep. 2006, p. 136-142.

(Continued)

*Primary Examiner* — David J Blanchard
*Assistant Examiner* — John P Nguyen
(74) *Attorney, Agent, or Firm* — One3 IP Management, PC; Dean G. Stathakis; Peter D. Weinstein

(57) ABSTRACT

The present invention is theobromine as an active agent to be delivered via the inhaled route, for the treatment of cough.

14 Claims, 2 Drawing Sheets

(56) References Cited

OTHER PUBLICATIONS

Usmani, Omar S. et al., Theobromine inhibits sensory nerve activation and cough. FASEB Journal, vol. Faseb-Journal-Express, Nov. 17, 2004, pp. 1-16.

Wangemann, G., Clinical experience with dyspnocedy an anti-asthma drug. Arztliche Wochenschrift, vol. 5, No. 17, 1950, pp. 272-273.

* cited by examiner

**P<0.01, *P<0.05

**P<0.01, *P<0.05

THEOBROMINE FOR THE TREATMENT OF COUGH

CROSS REFERENCE TO RELATED APPLICATION

This application is a National Stage Application of International Application Number PCT/GB2010/050997, filed Jun. 15, 2010; which claims priority to Great Britain Application No. 0910375.5, filed Jun. 16, 2009; all of which are incorporated herein by reference in their entirety.

FIELD OF THE INVENTION

This invention relates to theobromine and its use in the treatment of cough.

BACKGROUND OF THE INVENTION

Cough is a protective reflex. Persistent cough can be distressing. Over-the-counter remedies are available but their effectiveness is doubtful.

WO98/42322 discloses the use of theobromine for the treatment of cough, to be given orally. It shows the anti-tussive activity of oral theobromine which is directly correlated to its plasma concentration.

Usmani et al., FASEB J. express article 10.1096, discloses that theobromine inhibits sensory nerve action and cough. Data are provided, showing effects following oral dosing in citric-acid induced cough in the guinea pig, in the capsaicin cough challenge in humans, and following bathing of isolated guinea pig vagus nerve preparations.

SUMMARY OF THE INVENTION

The present invention relates to the use of theobromine by inhalation, in the treatment of cough.

The invention is based at least in part on data showing an equivalent anti-tussive effect for inhaled theobromine at ⅓ of the oral dose in a citric acid-induced cough model. Via the inhaled route, theobromine is surprisingly potent and does not follow the oral PK/PD relationship, revealing that theobromine has a substantially local effect in the lung. Consequently, via the inhaled route, less drug is given for an equivalent oral effect, so reducing side-effects and drug burden. Side-effects such as sedation can be minimised.

Theobromine can be used in combination or co-administration with a wide range of respiratory medicines, with little concern over systemic complications that may arise. Theobromine can be administered on a continued basis without concern over systemic side-effects (e.g. tachycardia). Theobromine can be administered on a once daily basis.

The present invention is therefore theobromine as an active agent to be delivered via the inhaled route, for the treatment of cough.

DESCRIPTION OF THE INVENTION

Figure 1:
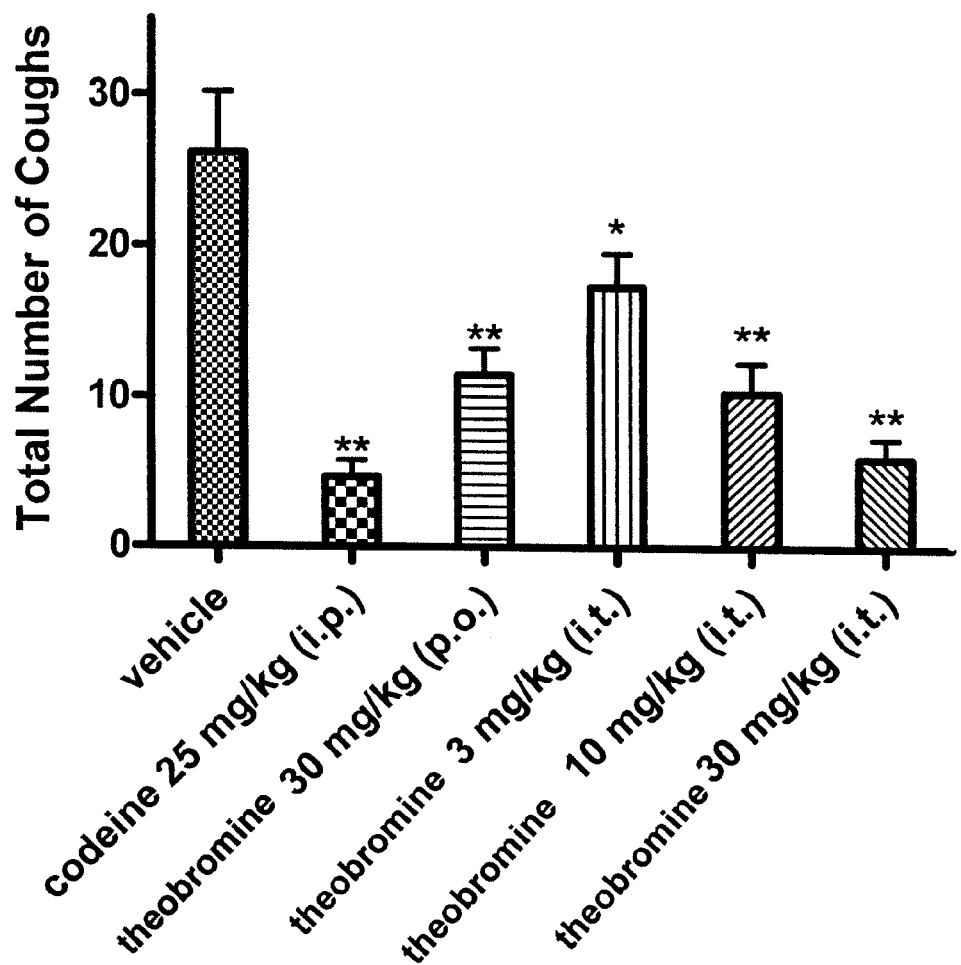
FIG. 1 is a graph showing the total number of coughs in guinea-pigs during a 10 minute exposure and 5 minute recovery period to citric acid (1M), following pre-treatment with either vehicle (i.t.), codeine (25 mg kg$^{-1}$, i.p.), or theobromine (3-30 mg/kg, i.t. or 30 mg/kg, p.o.) at t−30 min with respect to citric acid exposure. Each column represents the mean, and each vertical bar represents the s.e. mean. Changes in total cough number in the presence of theobromine or codeine were compared to vehicle treated animals using ANOVA followed by Dunnett's test to compare the means.

Any suitable form of the active agent can be chosen. These include salts, prodrugs and active metabolites.

Theobromine is to be administered via the inhaled route. Devices and formulations suitable for delivery by inhalation typically comprise particles of the active agent(s), and are generally known to the skilled person. In one embodiment, the composition may be prepared for delivery as an aerosol in a liquid propellant, for example for use in a pressurised or other metered dose inhaler (MDI). Propellants suitable for use in a PMDI are known to the skilled person, and include CFC-12, HFA-134a, HFA-227, HCFC-22 (difluorochloromethane), HFA-152 (difluoroethane and isobutane). Nebulisers and aerosol delivery systems are further alternatives.

In another embodiment, a composition of the invention is in dry powder form, for delivery using a dry powder inhaler (DPI). Dry powder inhalers are known. A dry powder for use in the inhalers will usually have a mass median aerodynamic diameter of less than 30 μm, preferably less than 20 μm and more preferably less than 10 μm. Microparticles having aerodynamic diameters in the range of 5 to 0.5 μm will generally be deposited in the respiratory bronchioles, whereas smaller particles, having aerodynamic diameters in the range of 2 to 0.05 μm, are likely to be deposited in the alveoli.

The DPI may be a passive dry powder inhaler, which relies on the patient's inspiration to introduce the particles into the lungs. Active inhalers, requiring a mechanism for delivering the powder to the patient, may also be used.

It will be appreciated that the particulate compositions are to be formulated in physiologically effective amounts. That is, when delivered in a unit dosage form, there should be a sufficient amount of the active agent to achieve the desired response. As the particles are intended primarily for delivery in dry powder inhalers, it will be appreciated that a unit dose comprises a predefined amount of particles delivered to a patient in one inspiratory effort. For guidance only, a single unit dose will be approximately 1 mg to 15 mg, preferably 5 mg to 10 mg of the particles.

The frequency of dosing can be selected by one of ordinary skill in the art. It may be, for example, once or twice daily, weekly or continuous.

The microparticles may also be formulated with additional excipients to aid delivery and release. For example, in the context of dry powder formulations, the microparticles may be formulated with additional large carrier particles which aid the flow from the dry powder inhaler into the lung. Large carrier particles are known, and include lactose particles having a mass median aerodynamic diameter of greater than 90 μm. Alternatively, or in addition, the microparticles may be dispersed within a carrier material. For example, the microparticles may be dispersed within a polysaccharide matrix, with the overall composition formulated as microparticles for direct delivery to the lung. The polysaccharide acts as a further barrier to the immediate release of the active component. This may further aid the controlled release process. Suitable carrier materials will be apparent to the skilled person and include any pharmaceutically acceptable insoluble or soluble material, including polysaccharides. An example of a suitable polysaccharide is xantham gum.

The compositions may also comprise additional therapeutic agents, either as separate components, i.e. as separate microparticles, or combined with the active agent in the microparticles.

Any suitable pharmaceutically effective drug which is used for the treatment of a respiratory disease may also be co-administered with agents/compositions of the invention. For example, $\beta_2$-agonists, e.g. salbutamol, salmeterol and formoterol, may be formulated for co-administration. Additional anti-muscarinic compounds may also be co-administered. For example, ipratropium (e.g. ipratropium bromide) or tiotropium may be administered.

Additional therapeutic agents, including steroids, may also be co-administered. Examples of suitable steroids include beclomethasone, dipropionate and fluticasone. Other suitable therapeutic agents suitable for co-administration include mucolytics, matrix metalloproteinase inhibitors, leukotrienes, antibiotics, anti-infective agents, antineoplastics, peptides, nicotine, PDE4-inhibitors, elastase inhibitors and sodium cromoglycate.

It is particularly preferred that theobromine should be used in combination with a bronchodilator. Suitable such agents are $\beta$-agonists, anti-muscarinics and PDE inhibitors.

Compositions according to the invention may be produced using conventional formulation techniques. In particular, spray-drying may be used to produce microparticles comprising the active agent dispersed or suspended within a material that provides the controlled release properties.

The process of milling, for example jet milling, may also be used to formulate the therapeutic composition. The manufacture of fine particles by milling can be achieved using conventional techniques. The term "milling" is used herein to refer to any mechanical process which applies sufficient force to the particles of active material to break or grind the particles down into fine particles. Various milling devices and conditions are suitable for use in the production of the compositions of the invention. The selection of appropriate milling conditions, for example, intensity of milling and duration, to provide the required degree of force, will be within the ability of the skilled person. Ball milling is a preferred method. Alternatively, a high pressure homogeniser may be used, in which a fluid containing the particles is forced through a valve at high pressure, producing conditions of high shear and turbulence. Shear forces on the particles, impacts between the particles and machine surfaces or other particles, and cavitation due to acceleration of the fluid, may all contribute to the fracture of the particles. Suitable homogenisers include the EmulsiFlex high pressure homogeniser, the Niro Soavi high pressure homogeniser and the Microfluidics Microfluidiser. The milling process can be used to provide the microparticles with mass median aerodynamic diameters as specified above. If hygroscopic, the active agent may be milled with a hydrophobic material, as stated above.

If it is required, the microparticles produced by the milling step can then be formulated with an additional excipient. This may be achieved by a spray-drying process, e.g. co-spray-drying. In this embodiment, the particles are suspended in a solvent and co-spray-dried with a solution or suspension of the additional excipient. Preferred additional excipients include polysaccharides. Additional pharmaceutically effective excipients may also be used.

Therapy according to the invention may be conducted in generally known manner, depending on various factors, such as the sex, age or condition of the patient, and the existence or otherwise of one or more concomitant therapies.

The amount of active ingredient in one unit dose may be, e.g. 0.02-250 mg, preferably less than 2 mg, most preferably less than or about 1 mg. Larger or smaller doses may also be provided, for example, less than 100 µg. In the particles, the active agent may be present in, for example, greater than 20% by weight, preferably greater than 40% by weight, and more preferably greater than 60% by weight.

In a preferred embodiment, the daily dose of theobromine is from 1 to 3000 mg. More preferably it is from 50 to 1500 mg, or from 400 to 1000 mg. It will be appreciated that synergistic effects from combinations of theobromine and a second active agent may allow the dose of theobromine to be lowered. This will be known to the skilled person.

The following Example provides evidence on which the present invention is based.

EXAMPLE

The aim of this Example is to provide an assessment of the antitussive activity of intra-tracheally (i.t.) or orally dosed (p.o.) administered theobromine (3-30 mg/kg) compared to the positive control codeine (25 mg/kg, i.p.) against irritant-induced cough responses.

Animals

Male Dunkin Hartley guinea pigs (350-550 g, supplied by Harlan UK Ltd) were used throughout the study.

Protocol

Thirty-six guinea pigs were randomly allocated to one of the six treatment groups (see Table 1) according to the blinding code. The blinding code was not revealed to the experimenter until coughs from all of the animals had been tallied.

Guinea pigs were dosed intra-tracheally with theobromine or vehicle, orally with theobromine and intra-peronteneally with codeine. All pre-treatments were administered at t−30 min prior to citric acid exposure.

Individual guinea pigs were placed in an exposure chamber with an airflow of 2 L/min at t−10 min prior to citric acid exposure to acclimatise.

At t=0 min, cough responses were induced by exposure to citric acid aerosol (1 M) generated by an ultrasonic nebuliser at a nebulisation rate of 0.6 mL/min for 10 min.

Coughs were counted throughout the 10 min citric acid exposure and for a further 5 min post exposure.

TABLE 1

Treatment groups for study 277 (n = 6 guinea pigs per group).

| Vehicle Group | Positive control group | Treatment group 1 | Treatment group 2 | Treatment group 3 | Treatment group 4 |
|---|---|---|---|---|---|
| | Codeine (25 mg/kg, i.p.), 0.5 h pretreatment | Theobromine (30 mg/kg, p.o.), 0.5 h pretreatment | Theobromine (3 mg/kg, i.t.), 0.5 h pretreatment | Theobromine (10 mg/kg, i.t.), 0.5 h pretreatment | Theobromine (30 mg/kg, i.t.), 0.5 h pretreatment |

Results

Figure 2:
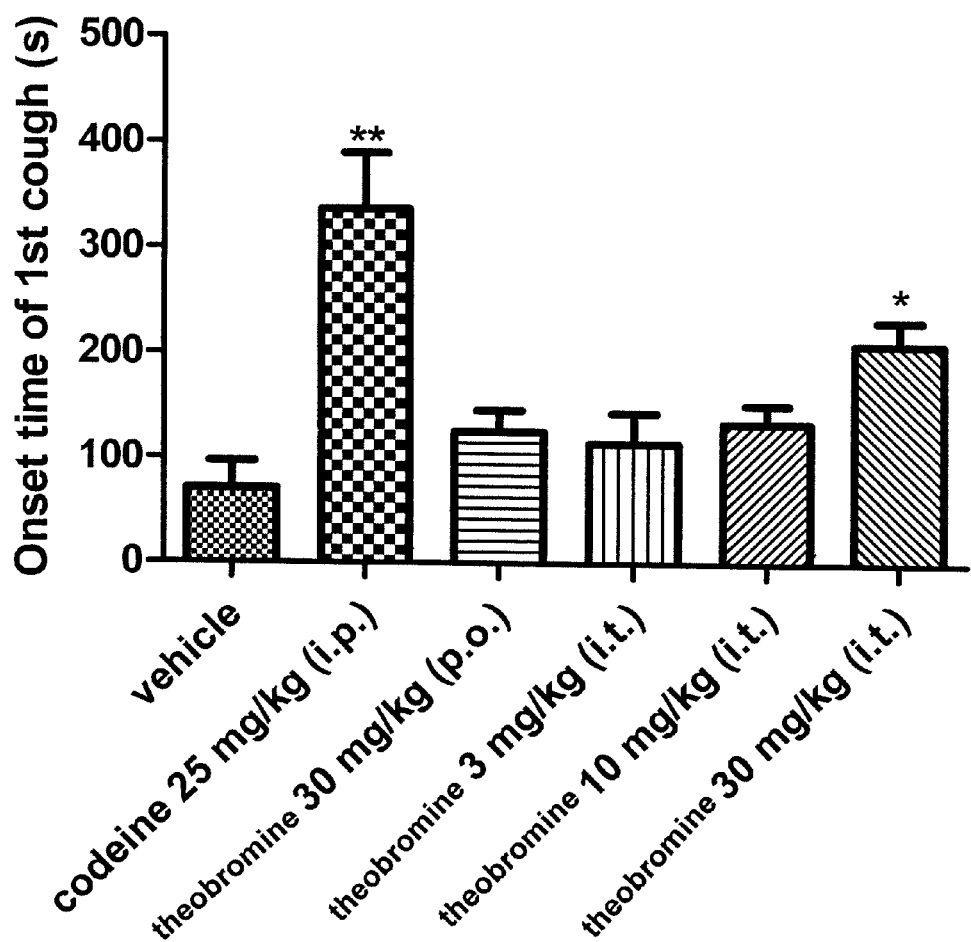
FIG. 2 is a graph showing the onset of coughs in guinea-pigs during a 10 minute exposure and a 5 minute recovery period to citric acid (1 M), following pre-treatment with either vehicle (i.t.), codeine (25 mg kg$^{-1}$, i.p.), or theobromine (3-30 mg/kg, i.t. or 30 mg/kg, p.o.) at t−30 min with respect to citric acid exposure. Each column represents the mean, and each vertical bar represents the s.e. mean. Changes in total cough number in the presence of theobromine or codeine were compared to sham dosed animals using ANOVA followed by Dunnett's test to compare the means.

The mean number of citric acid-induced cough responses recorded in the vehicle-treated guinea pigs was 26±4 coughs with a mean onset time for the first cough of 71±26 s. This level of response was significantly reduced to 5±1 coughs in codeine-treated animals, and the onset to the first cough was significantly extended to 337±51 s. Similarly, pre-treatment with theobromine (30 mg/kg, p.o.) also caused a significant reduction to the number of citric acid-induced coughs (12±2), although the onset to the first cough was not significantly increased beyond the time observed in the vehicle control animals. Local administration (i.t.) of theobromine also had a significant dose-dependant effect on the total number of coughs, reducing the number of coughs at a dose of 30 mg/kg of theobromine to 6±1. Indeed, at the doses of 10 mg/kg (i.t.), theobromine caused a similar effect to that observed at 30 mg/kg (p.o.) theobromine (10.33±2 coughs compared to 12±2 coughs respectively). It was also evident that, with increasing concentration of intra-tracheally administered theobromine, there was an increase to the onset of the first cough which was significantly increased with a dose of 30 mg/kg to 210±22 s (see FIGS. 1 and 2).

Observations

Dosing with theobromine (3-30 mg/kg, i.t.) and theobromine (30 mg/kg) caused no noticeable change in the behaviour and health of the animals. Codeine (25 mg/kg, i.p.) treated animals showed signs of slight sedation as was typified by a reduction in movement while in the exposure chamber.

The invention claimed is:

1. A method for treating a cough, said method comprising the step of: administering a composition comprising a physiological effective amount of an active agent and an excipient to a subject in need of such treatment, wherein the active agent consists of theobromine, wherein the composition is formulated for delivery via inhalation, wherein the amount of theobromine administered to the subject is less than 2 mg, and wherein administration of the composition reduces the number of coughs experienced by the subject.

2. The method according to claim 1, wherein delivery is achieved using a metered dose inhaler.

3. The method according to claim 1, wherein delivery is achieved using a dry powder delivery device.

4. The method according to claim 1, wherein delivery is achieved using a nebuliser.

5. The method according to claim 1, wherein the composition is dosed daily.

6. The method according to claim 1, wherein the composition is dosed weekly.

7. The method according to claim 1, wherein the amount of theobromine administered to the subject is between 0.02 mg and 2 mg.

8. The method according to claim 1, wherein the theobromine is in the form of particles having a mass median diameter of up to 10 µm.

9. The method according to claim 1, wherein the excipient includes a polysaccharide.

10. The method according to claim 1, wherein the amount of theobromine administered to the subject is less than 1 mg.

11. The method according to claim 1, wherein the amount of theobromine administered to the subject is between 0.02 mg and 1 mg.

12. The method according to claim 1, wherein the composition further comprises a propellant, a solvent, and water.

13. The method according to claim 1, wherein the composition is a dry powder.

14. The method according to claim 1, wherein the composition is an aerosol.

* * * * *